（12）United States Patent
Rao et al.

(10) Patent No.: US 10,528,240 B2
(45) Date of Patent: Jan. 7, 2020

(54) SYSTEM AND METHOD FOR IMAGE POST-PROCESSING AND VIEWING UTILIZING A REGION OF INTEREST

(71) Applicant: General Electric Company, Schenectady, NY (US)

(72) Inventors: Bellary Madhusudan Rao, Bangalore (IN); Vinay Chaugule, Bangalore (IN); Mahalingam Neelakantan, Bangalore (IN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 114 days.

(21) Appl. No.: 15/806,709

(22) Filed: Nov. 8, 2017

(65) Prior Publication Data

US 2019/0138192 A1    May 9, 2019

(51) Int. Cl.
| | |
|---|---|
| G06F 3/048 | (2013.01) |
| G06F 3/0484 | (2013.01) |
| G06F 3/0354 | (2013.01) |
| G06T 7/00 | (2017.01) |

(52) U.S. Cl.
CPC ...... *G06F 3/04845* (2013.01); *G06F 3/03543* (2013.01); *G06F 3/04842* (2013.01); *G06F 3/04847* (2013.01); *G06T 7/0012* (2013.01); *G06T 2200/24* (2013.01); *G06T 2207/20024* (2013.01); *G06T 2207/20104* (2013.01)

(58) Field of Classification Search
None
See application file for complete search history.

(56) References Cited

U.S. PATENT DOCUMENTS

| | | | |
|---|---|---|---|
| 6,463,181 B2 | 10/2002 | Durate | |
| 8,233,690 B2 | 7/2012 | Ng et al. | |
| 2007/0294634 A1* | 12/2007 | Kokemohr | G06F 3/04845 715/781 |
| 2009/0024440 A1 | 1/2009 | Spahn | |
| 2011/0123086 A1* | 5/2011 | Nie | G06T 5/003 382/132 |
| 2012/0172700 A1 | 7/2012 | Krishnan et al. | |
| 2013/0016890 A1 | 1/2013 | Lee et al. | |

(Continued)

OTHER PUBLICATIONS

Navpreet Kaur et al., Mouse Cursor Control System Based on SSVEP, Jul. 2017, International Journal of Advanced Reseaqrch in Computer Science, vol. 8 No. 7, pp. 162-167 (Year: 2017).*

(Continued)

*Primary Examiner* — Tam T Tran
(74) *Attorney, Agent, or Firm* — Fletcher Yoder, P.C.

(57) ABSTRACT

A method is provided. The method includes utilizing a processor to: load image data on a user interface, receive a first input selecting a particular mode to view the image data in on the user interface that causes display of an image derived from the image data on the user interface on a display, receive a second input, via a scroll wheel of a computer mouse, selecting a type of image that causes display in only a region of interest (ROI) of the selected type of image on the user interface on the display while a remainder of the image outside the ROI is displayed at a default state, and receive a third input, via a button the computer mouse, that causes application of the selected type of image to the entire image displayed on the user interface on the display.

20 Claims, 15 Drawing Sheets

(56) References Cited

U.S. PATENT DOCUMENTS

| | | | | |
|---|---|---|---|---|
| 2013/0207997 A1* | 8/2013 | Berger | .................... | G06T 11/60 |
| | | | | 345/619 |
| 2013/0329994 A1* | 12/2013 | Webb | ....................... | G09G 5/02 |
| | | | | 382/167 |
| 2015/0371422 A1* | 12/2015 | Kokemohr | .............. | G06T 11/60 |
| | | | | 382/311 |

OTHER PUBLICATIONS

Joshua Abbott et al., Interactive Depth-Aware Effects for Stereo Image Editing, Jun. 1, 2013, IEEE Computer Society, pp. 263-270 (Year: 2013).*

Mariani, Caterina, et al.; "Analysis of the X-ray Work Flow in Two Diagnostic Imaging Departments With and Without a RIS/PACS System", Journal of Digital Imaging, vol. 19, Supp 1, 2016; pp. 18-28.

Brun, Francesco, et al.; "SYRMEP Tomo Project: a graphic user interface for customizing CT reconstruction workflows", Advanced Structural and Chemical Imaging, 2017 pp. 1-9.

Suni; Dental and Medical Digital X-Ray Imaging Software; 2017; http://www.suni.com/products/drsuni.aspx.

Suni; Dental and Medical Digital X-Ray Imaging Software; 2017; http://www.suni.com/products/profsuni.aspx.

Thomas, Maikael A., et al.; "Interactive Image Enhancement of CR and DR Images", Journal of Digital Imaging, vol. 17, No. 3, Sep. 2004; pp. 189-195.

* cited by examiner

SYSTEM AND METHOD FOR IMAGE POST-PROCESSING AND VIEWING UTILIZING A REGION OF INTEREST

BACKGROUND

The subject matter disclosed herein relates to medical imaging and, in particular, to utilizing a region of interest (ROI) to optimize the work flow for image post-processing and viewing.

After the acquisition of medical image data utilizing a medical imaging system (e.g., computed tomography (CT) system, magnetic resonance (MR) imaging, ultrasound system, etc.) a user may analyze the image data. Analysis of the image data may involve manipulating the image data by performing post-processing procedures and/or altering the view of the image. For example, images may be loaded into an image viewer or user interface that enables the user to alter the image (e.g., apply a post-processing filter) or reformat the image. However, the workflow for typically altering or reformatting these images may be labor intensive and not user friendly.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a method is provided. The method includes utilizing a processor to: load image data on a user interface, receive a first input selecting a particular mode to view the image data in on the user interface that causes display of an image derived from the image data on the user interface on a display, receive a second input, via a scroll wheel of a computer mouse, selecting a type of image that causes display in only a region of interest (ROI) of the selected type of image on the user interface on the display while a remainder of the image outside the ROI is displayed at a default state, and receive a third input, via a button the computer mouse, that causes application of the selected type of image to the entire image displayed on the user interface on the display.

In accordance with a second embodiment, a computer-readable medium is provided. The computer-readable medium includes processor-executable code to: load image data on a user interface, receive a first input selecting a particular mode to view the image data in on the user interface that causes display of an image derived from the image data on the user interface on a display, receive a second input, via a scroll wheel of a computer mouse, selecting a type of image that causes display in only a region of interest (ROI) of the selected type of image on the user interface on the display while a remainder of the image outside the ROI is displayed at a default state, and receive a third input, via a button the computer mouse, that causes application of the selected type of image to the entire image displayed on the user interface on the display.

In accordance with a third embodiment, a system is provided. The system includes a display, a processor, and a memory. The memory stores processor-executable code that when executed by the processor causes: loading image data on a user interface, receiving a first input selecting a particular mode to view the image data in on the user interface that causes display of an image derived from the image data on the user interface on a display, receiving a second input, via a scroll wheel of a computer mouse, selecting a type of image that causes display in only a region of interest (ROI) of the selected type of image on the user interface on the display while a remainder of the image outside the ROI is displayed at a default state, and receiving a third input, via a button the computer mouse, that causes application of the selected type of image to the entire image displayed on the user interface on the display

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Disclosed herein are systems and methods for providing an optimized workflow for medical image post-processing and viewing that utilizes a ROI of the image. The image data may be acquired/reconstructed via any medical imaging system (e.g., computed tomography (CT) system, magnetic resonance (MR) imaging, ultrasound system, etc.). In certain embodiments, once an image or images is loaded into an image viewer or user interface a user (e.g., radiologist) may utilize a user input device (e.g., mouse) to optimize the workflow (e.g., ROI based workflow) in performing post-processing procedures and/or altering the view of the image. Utilization of the ROI in conjunction with manipulation of the mouse enables an improvement in the workflow time. The ROI based workflow utilizes a ROI that is smaller than the image that enables the post-processing to only be applied to the ROI as opposed to the entire image. In certain embodiments, the ROI based workflow may be utilized in applying and/or selecting filters for the image. In other embodiments, the ROI based workflow may be utilized in switching between images acquired/reconstructed at different energies (e.g., keV) for the same patient. In certain embodiments, the ROI based workflow may be utilized in switching between different material decomposed images (e.g., material differentiated images) for the same patient.

Figure 1:
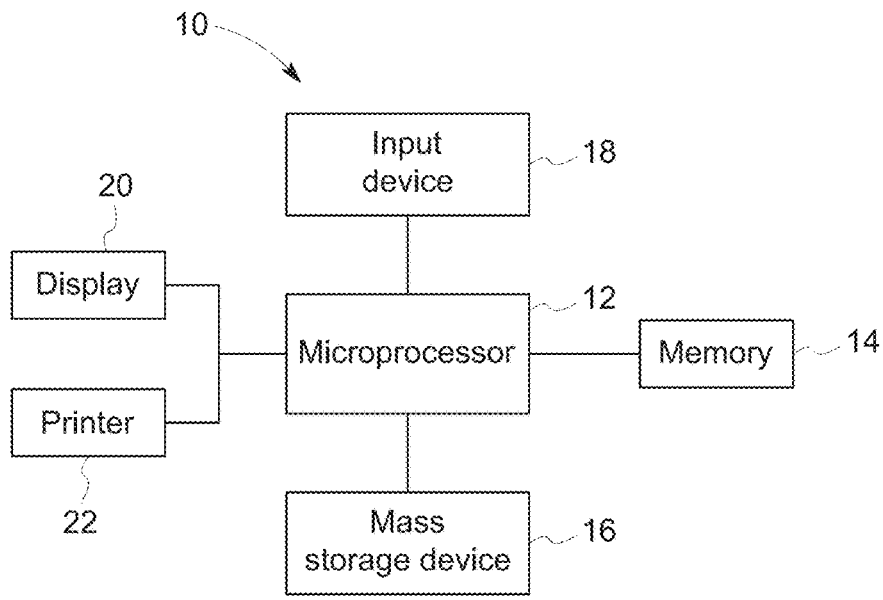
FIG. 1 is a block diagram of a processor-based device or system that may be configured to implement functionality described herein in accordance with one embodiment.

FIG. 1 is a block diagram of a processor-based device or system that may be configured to implement functionality described herein in accordance with one embodiment. Various functionality, including medical image post-processing and viewing utilizing a ROI described herein, may be performed by, or in conjunction with, a processor-based system 10, which is generally depicted in FIG. 1 in accordance with one embodiment. For example, the various controllers and circuitry discussed herein may include, or be partially or entirely embodied in, a processor-based system, such as that presently illustrated. The processor-based system 10 may be a general-purpose computer, such as a personal computer, configured to run a variety of software, including software implementing all or part of the functionality described herein. Alternatively, in other embodiments, the processor-based system 10 may include, among other things, a distributed computing system, or an application-specific computer or workstation configured to implement all or part of the presently described functionality based on specialized software and/or hardware provided as part of the system. Further, the processor-based system 10 may include either a single processor or a plurality of processors to facilitate implementation of the presently disclosed functionality.

In one embodiment, the exemplary processor-based system 10 includes a microcontroller or microprocessor 12, such as a central processing unit (CPU), which executes various routines and processing functions of the system 10. For example, the microprocessor 12 may execute various operating system instructions, as well as software routines configured to effect certain processes, stored in or provided by a manufacture including one or more computer readable-media (at least collectively storing the software routines), such as a memory 14 (e.g., a random access memory (RAM) of a personal computer) or one or more mass storage devices 16 (e.g., an internal or external hard drive, a solid-state storage device, a CD-ROM, a DVD, or another storage device). In addition, the microprocessor 12 processes data provided as inputs for various routines or software programs, such as data provided as part of the present subject matter described herein in computer-based implementations.

Such data may be stored in, or provided by, the memory 14 or mass storage device 16. Alternatively, such data may be provided to the microprocessor 12 via one or more input devices 18. The input devices 18 may include manual input devices, such as a keyboard, a mouse, touchscreen (e.g., on tablet), or the like. In a preferred embodiment, the input device includes a computer mouse having at least a button and a scroll wheel to provide user input to the microprocessor 12. Any inputs received described below may be made with either the button or scroll wheel of the mouse or any other type of input device (e.g., keyboard, touchscreen, etc.). In addition, the input devices 18 may include a network device, such as a wired or wireless Ethernet card, a wireless network adapter, or any of various ports or devices configured to facilitate communication with other devices via any suitable communications network, such as a local area network or the Internet. Through such a network device, the system 10 may exchange data and communicate with other networked electronic systems, whether proximate to or remote from the system 10.

Results generated by the microprocessor 12, such as the results obtained by processing data in accordance with one or more stored routines, may be provided to an operator via one or more output devices, such as a display 20 and/or a printer 22. Based on the displayed or printed output, an operator may request additional or alternative processing or provide additional or alternative data, such as via the input device 18. Communication between the various components of the processor-based system 10 may typically be accomplished via a chipset and one or more busses or interconnects which electrically connect the components of the system 10. In one embodiment, the exemplary processor-based system 10 can be configured to, among other things, receive image data and load it in an image viewer or graphical user interface (GUI), enable post-processing and image viewing in the image viewer or GUI utilizing the ROI, and output the image data after post-processing.

Figure 2:
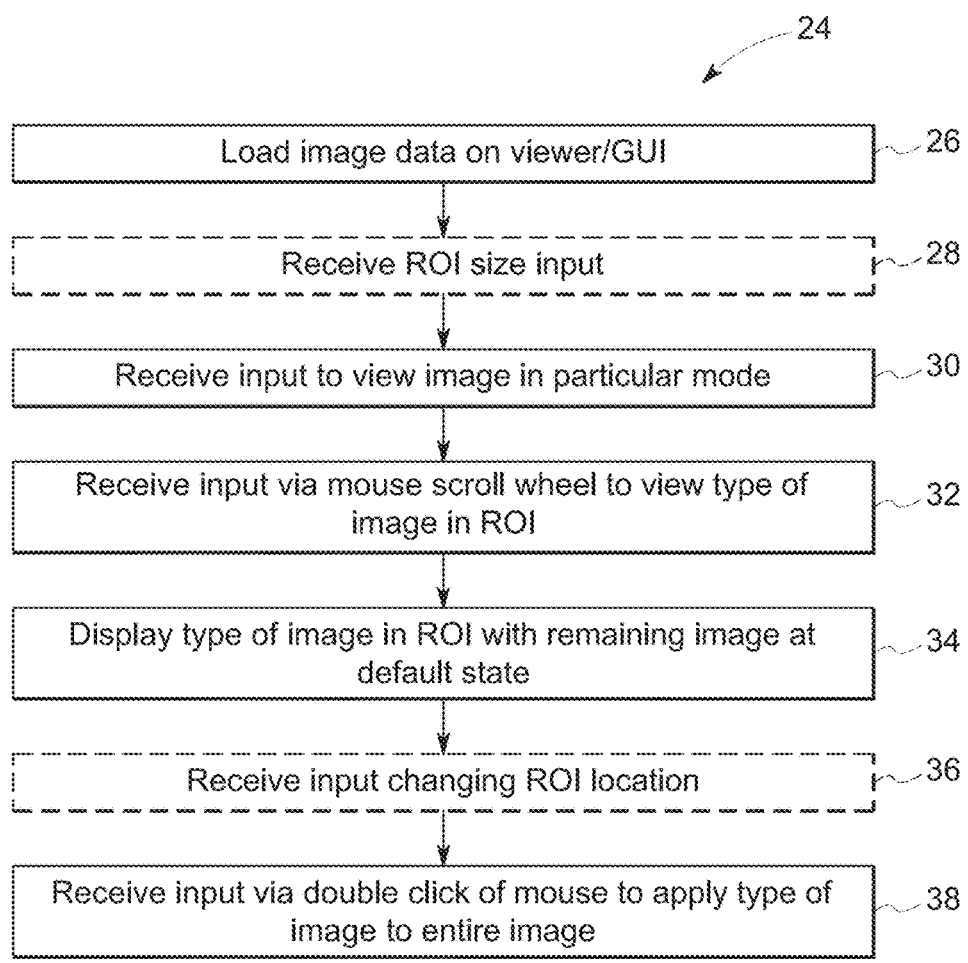
FIG. 2 is a flow chart of an embodiment of a method for optimization of image post-processing and viewing utilizing a region of interest (ROI)

FIG. 2 is a flow chart of an embodiment of a method 24 for optimization of image post-processing and viewing utilizing a ROI. One or more of the steps of the method 24 may be performed by the processor 12 of the system 10. One or more of the steps of method 24 may be performed simultaneously and/or in a different order from the order depicted in FIG. 2. The method 24 includes loading image data (e.g., one or more images) from a patient into an image viewer or GUI that enables post-processing and/or manipulation of the view of the image data (block 26). In certain embodiments, the processor 12 may receive a user input (e.g., via input device 18) selecting a size of the ROI (e.g., smaller than the entire image) to utilize (block 28). The shape of the ROI may be a square, rectangle, circle, or any other shape. In certain embodiments, the ROI may be tagged with labels that include information displayed around a periphery of the ROI. For example, the information may include a mean, standard deviation, filter, keV, window length/width, or other information. The method 24 also includes receiving a user input (e.g., via input device 18) to view the image data (e.g., image) in a particular mode (block 30) in the image view or GUI. In certain embodiments, the mode may include a filtering mode that enables a user to select between different filters to apply the ROI and subsequently apply a desired or selected filter to the entire image. In certain embodiments, the mode may include a multi-kiloelectron volt (keV) overlay mode that enables switching between images acquired/reconstructed at different energies (e.g., keV) for the same patient for display in the ROI. In certain embodiments, the mode may include a material differentiation overlay mode that enables switching between different material decomposed images (e.g., material differentiated images) acquired for the same patient for display in the ROI. Once a particular mode is selected, the image (e.g., a quality check image) is displayed in the image viewer or GUI (e.g., on display 20). In addition, the ROI is also displayed on the image. The location of the ROI is determined by the location of the mouse pointer on the image viewer or GUI. The location of the ROI may be changed by a user by moving the mouse pointer (via the mouse) over the image.

The method 24 further includes receiving a user input, via a scroll wheel of the mouse, to view a type of image in the ROI (block 32). The type of image may include a particular filter applied to the ROI and rotating the scroll wheel of the mouse may result in switching between different filters applied on the ROI. In certain embodiments, the type of image may include an image acquired/reconstructed at a particular keV for the patient and rotating the scroll wheel of the mouse may result in switching between images acquired/reconstructed at different keVs for the same patient for display in the ROI. In certain embodiments, the type of image may include a particular material decomposed image acquired/reconstructed for the patient and rotating the scroll wheel of the mouse may result in switching between material decomposed images for different materials (e.g., monochromatic, water, iodine, etc.) for the same patient for display in the ROI. The method 24 includes displaying the type of image (e.g., particular filter, keV acquired/reconstructed image, material decomposition image, etc.) in the ROI on the image viewer or GUI, while the rest of the image outside the ROI is at a default state (block 34). The default state may include a quality check image (e.g., image acquired at particular keV) or a monochromatic image. In certain embodiments, the method 24 includes changing the location of the ROI by moving the mouse pointer (via the mouse) over the image (block 36). This enables the user to view the particular type of images in a different location on the image. The method 24 further includes receiving a user input, via a double click of a mouse button, to apply the type of image (e.g., particular filter, keV acquired/reconstructed image, material decomposition image, etc.) to the entire image (block 38).

Figure 3:
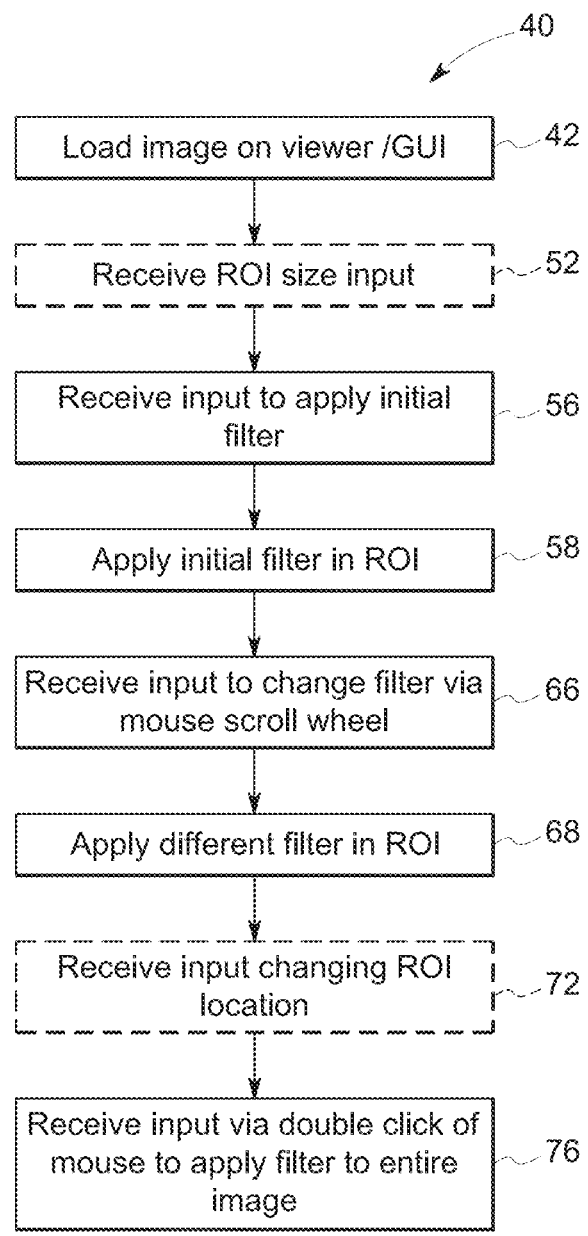
FIG. 3 is a flow chart of an embodiment of a method for optimization of image post-processing and viewing utilizing a ROI (e.g., for filtering)
Figure 4:
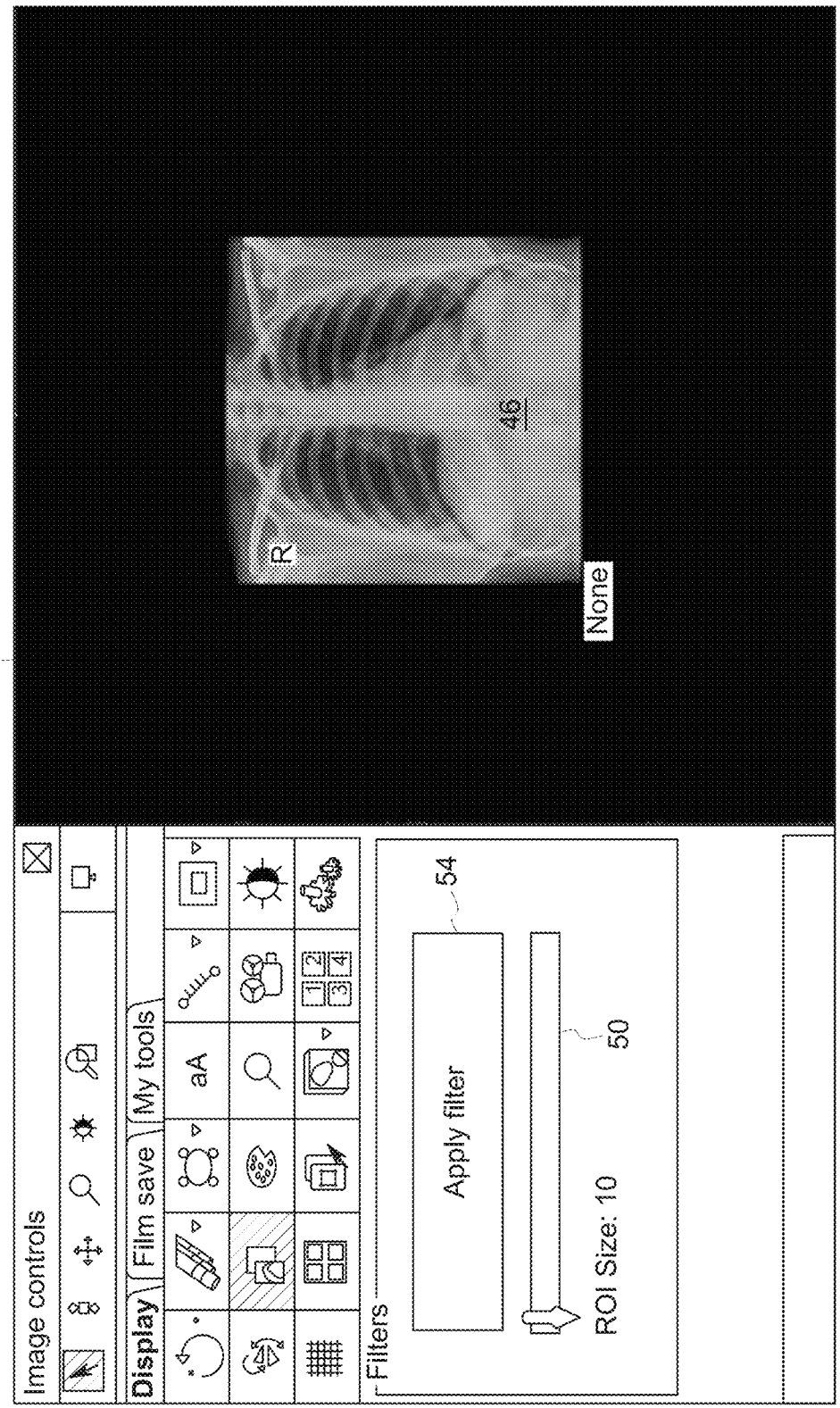
FIG. 4 is an embodiment of a display of a user interface utilizing the method of FIG. 3 (e.g., before filtering)
Figure 5:
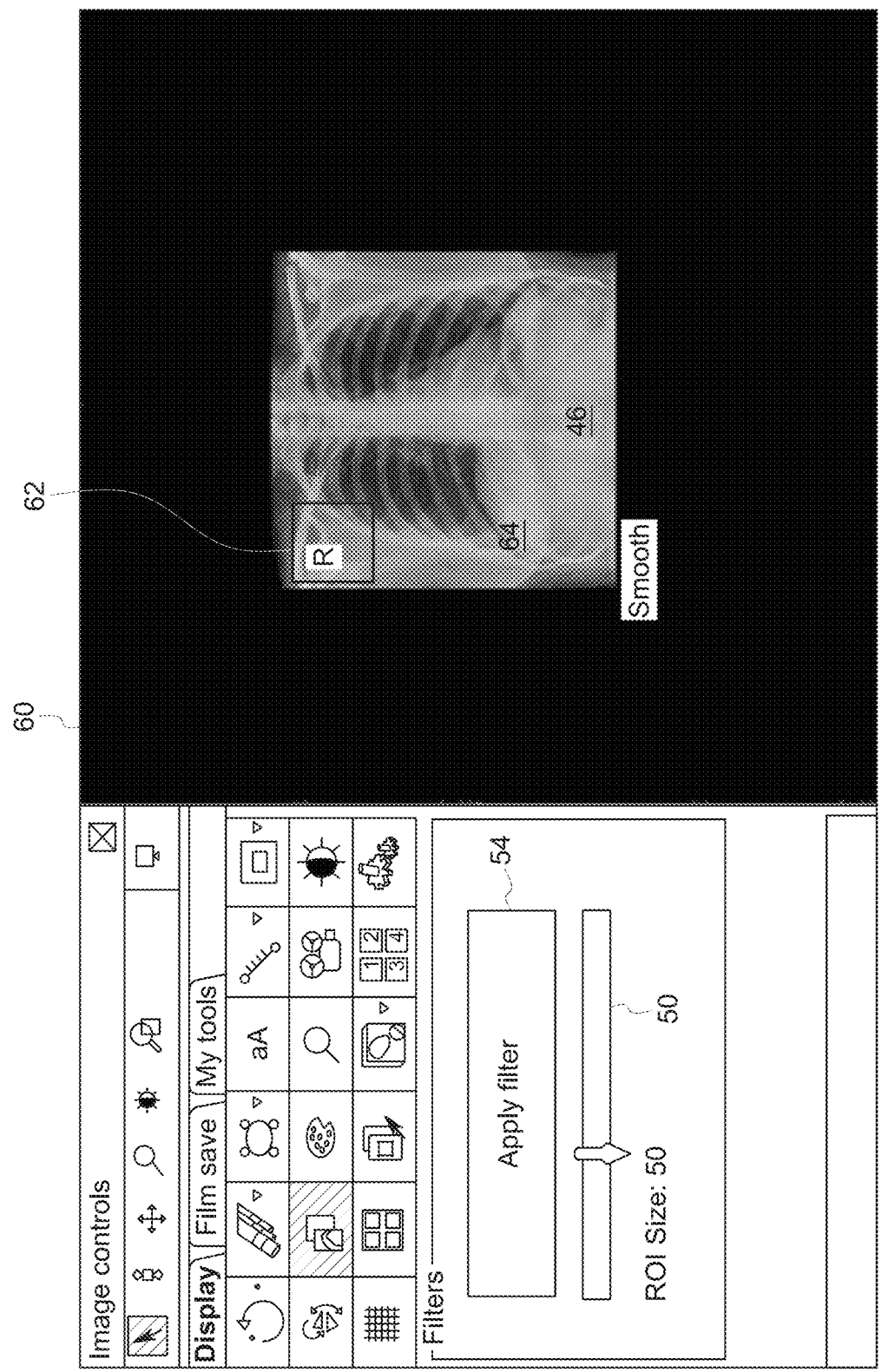
FIG. 5 is an embodiment of a display of a user interface utilizing the method of FIG. 3 (e.g., after filtering)
Figure 6:
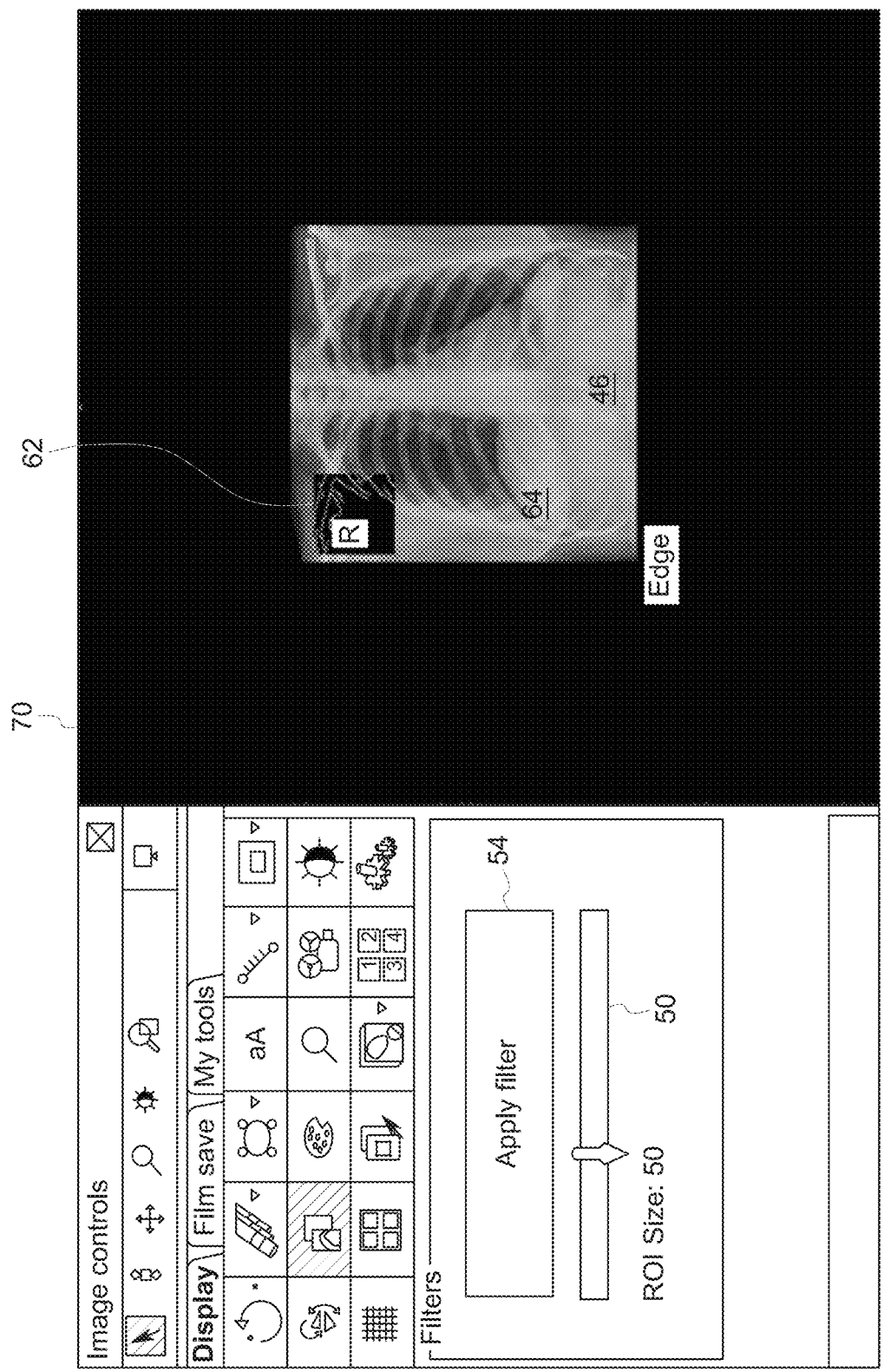
FIG. 6 is an embodiment of a display of a user interface utilizing the method of FIG. 3 (e.g., changing a filter)
Figure 7:
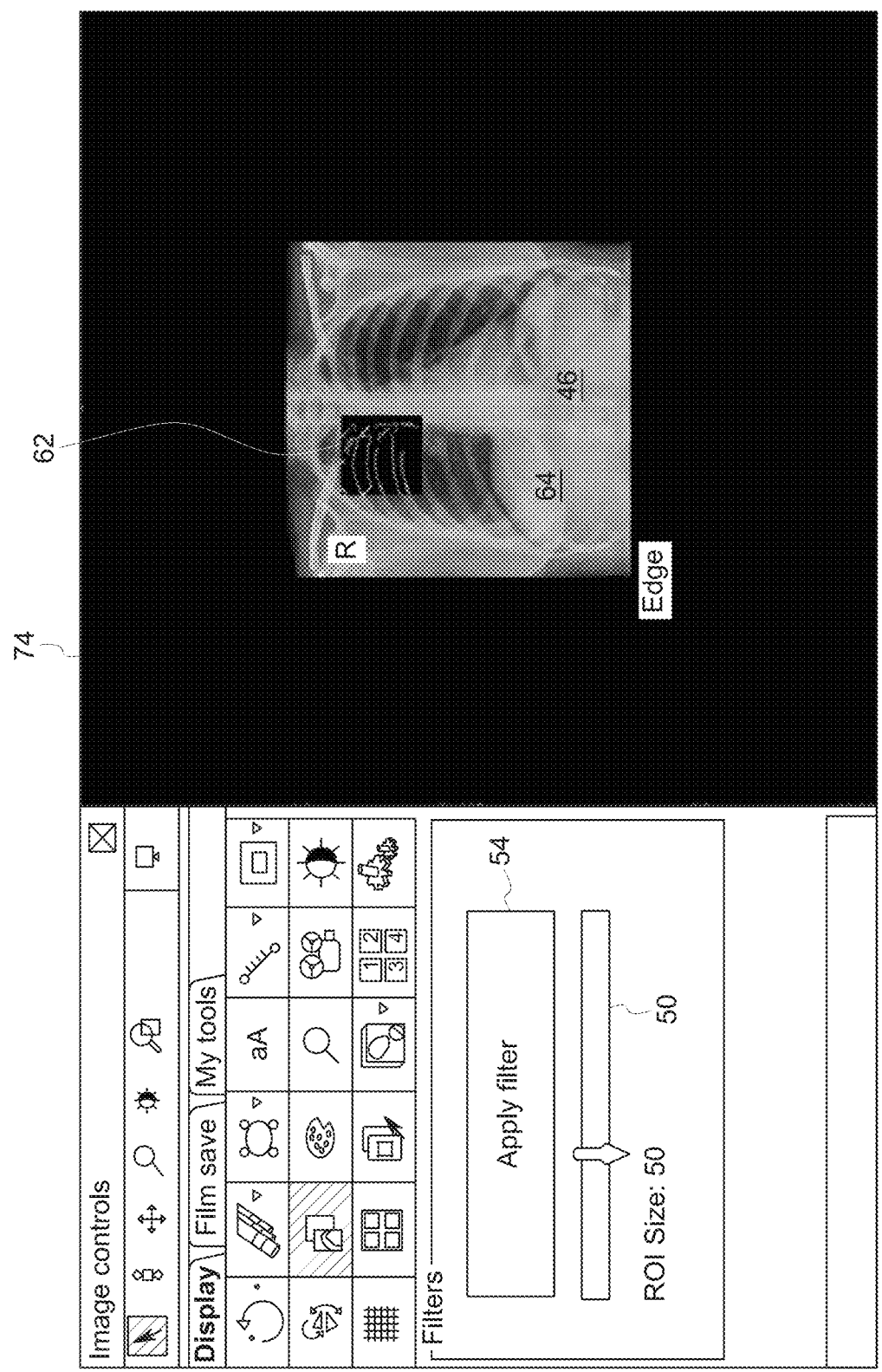
FIG. 7 is an embodiment of a display of a user interface utilizing the method of FIG. 3 (e.g., moving the ROI)
Figure 8:
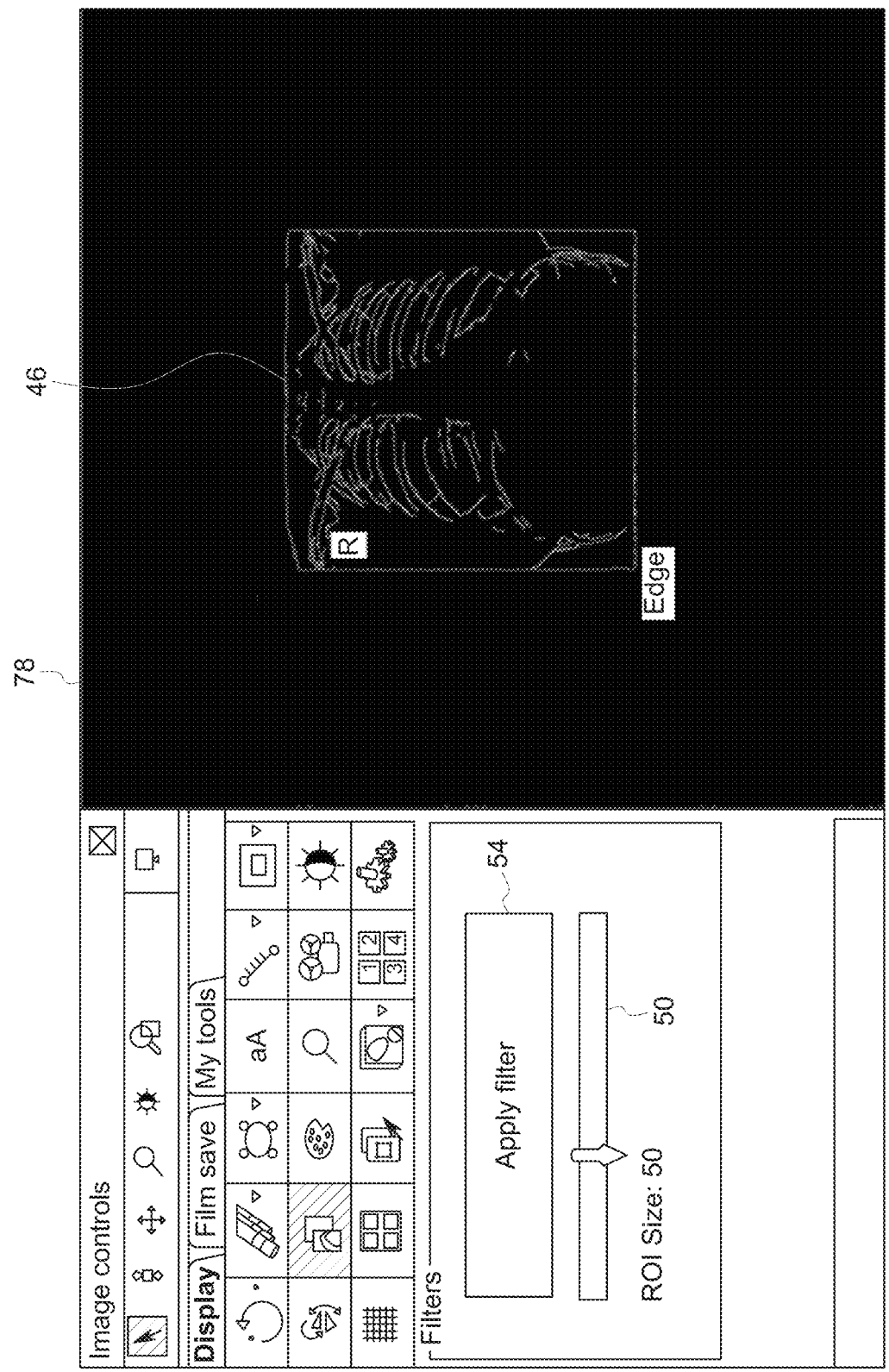
FIG. 8 is an embodiment of a display of a user interface utilizing the method of FIG. 3 (e.g., applying filter to entire image)

FIG. 3 is a flow chart of an embodiment of a method 40 for optimization of image post-processing and viewing utilizing a ROI (e.g., for filtering). One or more of the steps of the method 40 may be performed by the processor 12 of the system 10. One or more of the steps of method 40 may be performed simultaneously and/or in a different order from the order depicted in FIG. 3. The method 40 includes loading image data (e.g., an image) from a patient into an image viewer or GUI that enables post-processing and/or manipulation of the view of the image data (block 42). FIG. 4 depicts an example of a display 44 of a user interface displaying the image 46 before the application of a filter. An indicator located below and to the left of the image 46 indicates the filter status (i.e., what filter, if any, is applied to the ROI). In certain embodiments, the method 40 includes receiving a user input, via the input device 18 (e.g., on the ROI size bar 50 in FIG. 4), to select or change the size of the ROI (block 52). The method 40 also includes receiving a user input, via the input device 18 (e.g., "Apply Filter" icon 54 in FIG. 4) to apply an initial filter to the ROI (block 56). As noted above, the location of the ROI on the image will be determined via the location of the mouse pointer on the image. The method 40 further includes applying the filter only to the ROI, while the rest of the image outside the ROI does not have a filter applied (block 58). FIG. 5 depicts an example of a display 60 that shows the initial filter (e.g., smooth filter) applied to the ROI 62, while the rest of the image 64 outside the ROI does not have a filter applied. The method 40 includes receiving a user input, via rotation of a scroll wheel of the computer mouse, to change the filter applied to the ROI 62 (block 66). The method 40 also includes applying the different selected filter to only the ROI 62 (block 68). FIG. 6 depicts an example of a display 70 that shows a different filter (e.g., edge filter) applied to the ROI 62. In certain embodiments, the method 40 includes changing the location of the ROI 62 by moving the mouse pointer (via the mouse) over the image 46 (block 72). FIG. 7 depicts an example of a display 74 that shows the ROI 62 located in a different location due to movement of the mouse pointer. The method 40 further includes receiving a user input, via a double click of a mouse button, to apply the current filter applied to the ROI 62 to the entire image 46 (block 76). FIG. 8 depicts an example of a display 78 that shows the current filter (e.g., edge filter) applied to the entire image 46.

In contrast to the disclosed embodiment, typically a user would have to select a filter by selecting a filter option button on the user interface and the filter is applied to the entire image. Every time a filter is changed, a user would have to return to the user interface to select a different filter option button among the different filter option buttons. As result, workflow time is increased. In addition, since the selected filter is applied to the entire image, the user has no means to verify the effect of the filter on a local ROI. Utilization of the ROI in conjunction with manipulation of the mouse enables an improvement in the workflow time.

Figure 9:
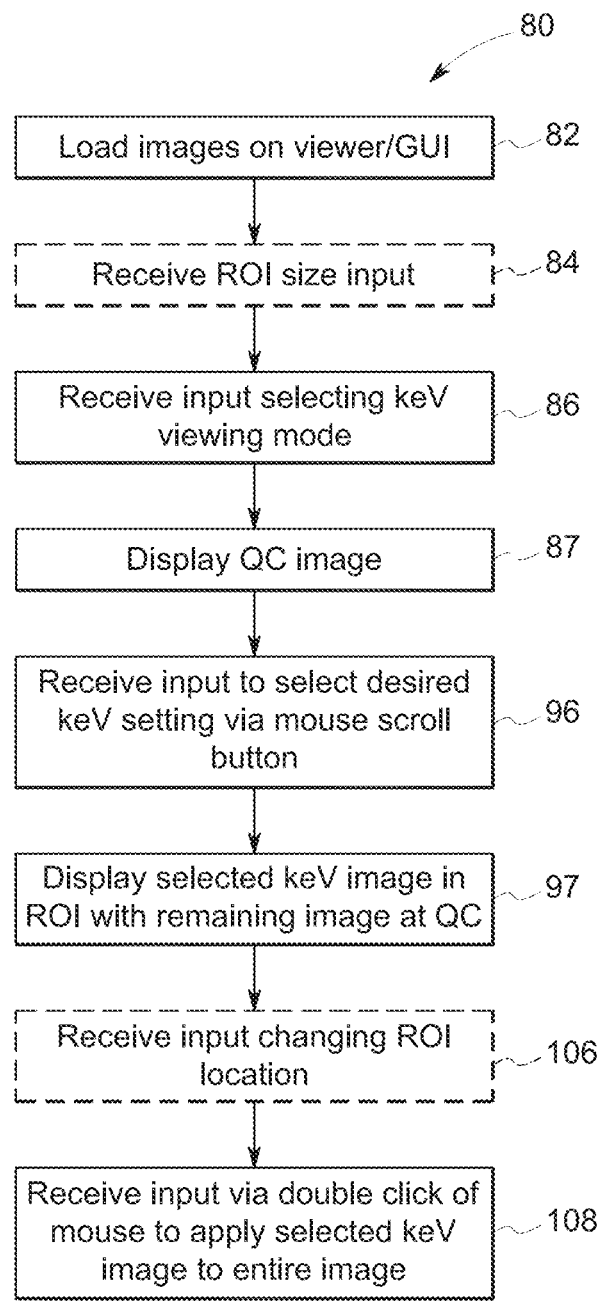
FIG. 9 is a flow chart of an embodiment of a method for optimization of image post-processing and viewing utilizing a ROI (e.g., for images acquired/reconstructed at different energies (keV)
Figure 10:
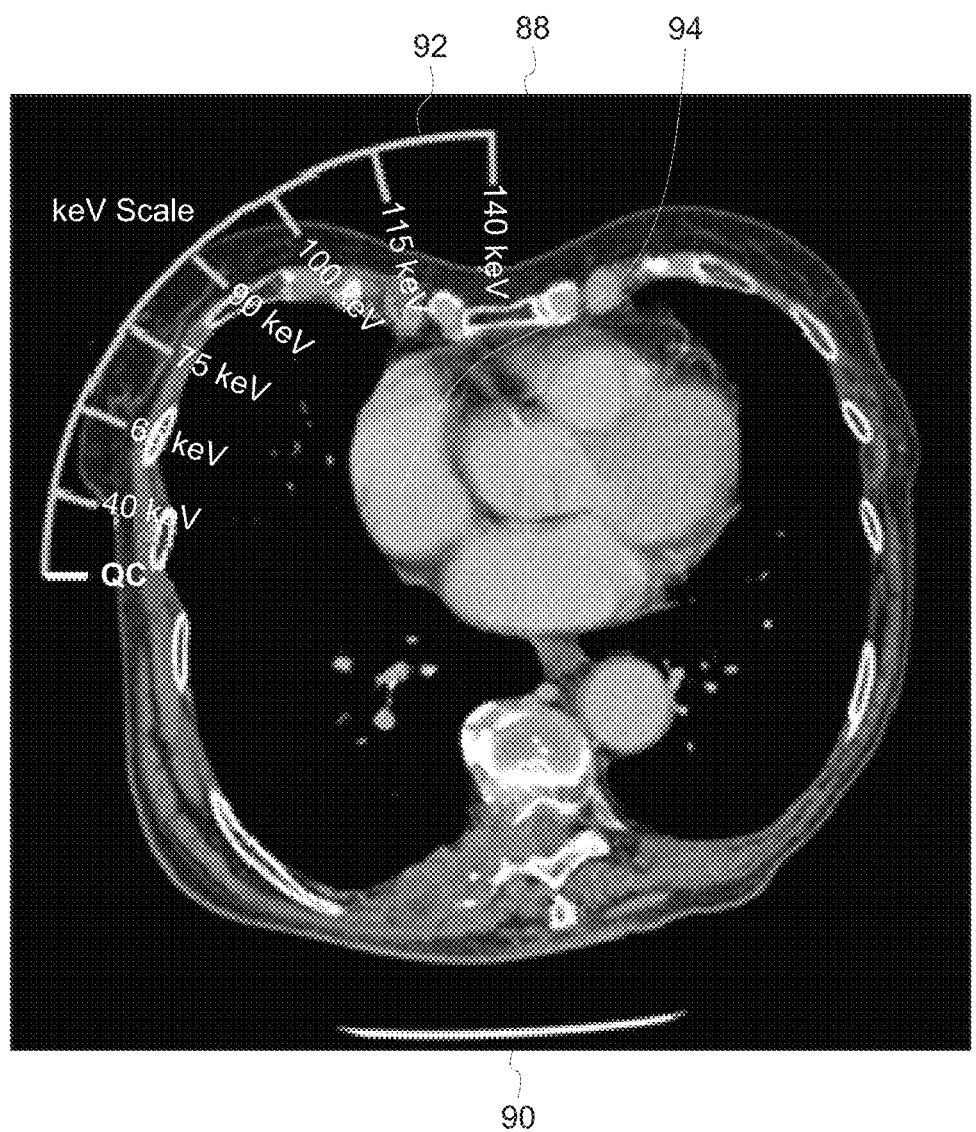
FIG. 10 is an embodiment of a display of a user interface utilizing the method of FIG. 9 (e.g., quality check image)

FIG. 9 is a flow chart of an embodiment of a method 80 for optimization of image post-processing and viewing utilizing a ROI (e.g., for images acquired/reconstructed at different energies (keV)). One or more of the steps of the method 80 may be performed by the processor 12 of the system 10. One or more of the steps of method 80 may be performed simultaneously and/or in a different order from the order depicted in FIG. 9. The method 80 includes loading image data (e.g., one or more images acquired/reconstructed at different energies) from a patient into an image viewer or GUI that enables post-processing and/or manipulation of the view of the image data (block 82). In certain embodiments, the method 80 includes receiving a user input, via the input device 18, to select or change the size of the ROI (block 84). The method 80 also includes receiving a user input, via the input device 18 selecting keV viewing mode for viewing the image in a mode that enables the user to select between different images from the same patient acquired/reconstructed at different energies for displaying in the ROI (block 86). As noted above, the location of the ROI on the image will be determined via the location of the mouse pointer on the image. The method 80 includes displaying the image (e.g., quality check image) in the keV viewing mode (block 87). FIG. 10 depicts an example of a display 88 of a user interface displaying the image 90. The image 90 in FIG. 10 depicts a quality check image (e.g., acquired at a particular kVp different from those displayed on the keV scale). A scale 92 (e.g., keV scale) representing different acquisition energies is superimposed over the image 90. A user may select a particular energy (or quality check image) from the scale 92, via the scroll wheel of the mouse, to display in the ROI 94 the image acquired/reconstructed at the selected energy. As depicted in FIG. 10, QC (quality check) is selected on the scale 92. Thus, the ROI 94 also displays the quality check image.

Figure 11:
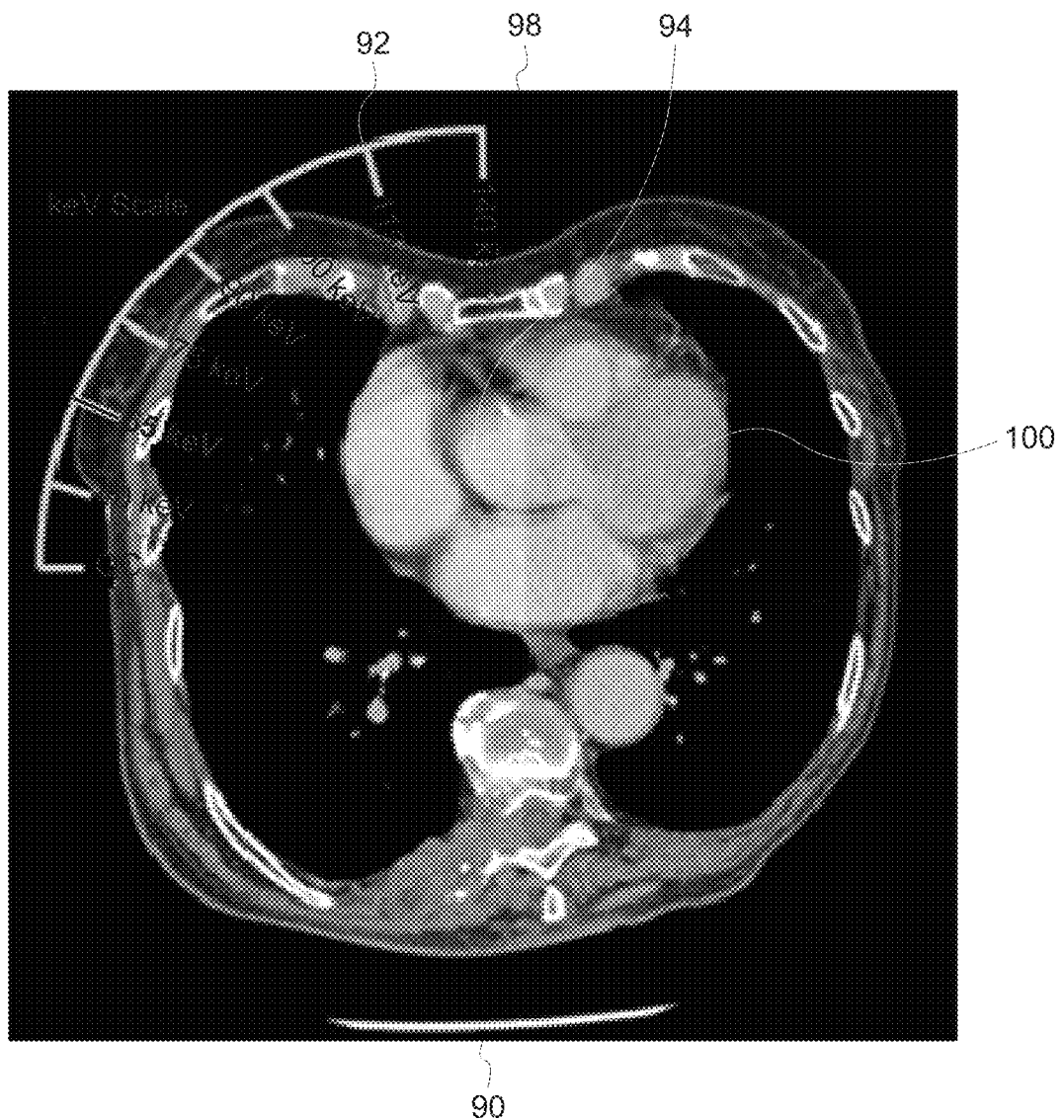
FIG. 11 is an embodiment of a display of a user interface utilizing the method of FIG. 9 (e.g., a first keV)
Figure 12:
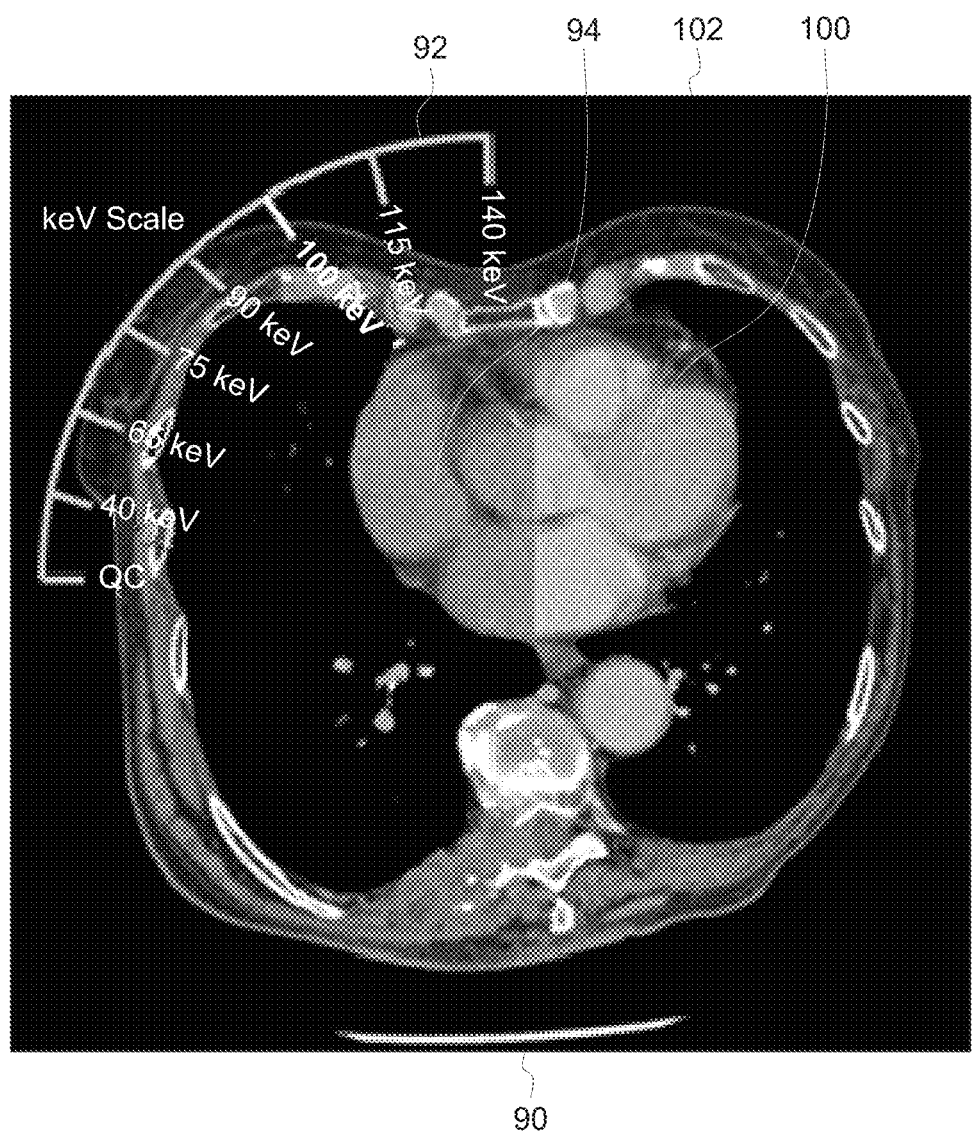
FIG. 12 is an embodiment of a display of a user interface utilizing the method of FIG. 9 (e.g., a second keV)
Figure 13:
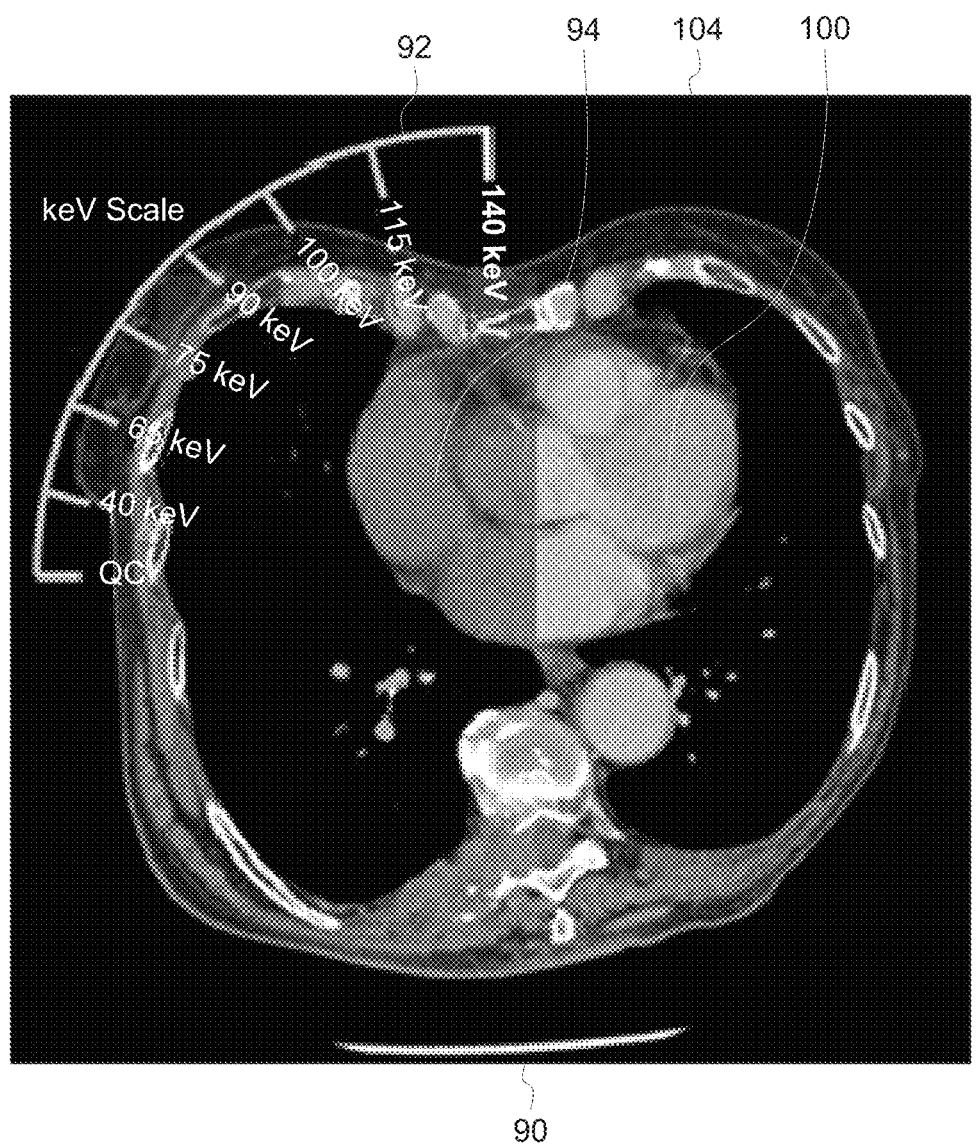
FIG. 13 is an embodiment of a display of a user interface utilizing the method of FIG. 9 (e.g., a third keV)

The method 80 includes receiving a user input, via rotation of the scroll wheel of the computer mouse, to change the desired energy on the scale 92 (block 96). The method 80 also includes displaying only in the ROI 94 the image of the patient acquired/reconstructed at the selected energy while the rest of the image remains the quality check image (block 97). FIG. 11 depicts an example of a display 98 that shows the ROI 94 of the image 90 including the image acquired/reconstructed at the selected energy (e.g., 65 keV) and the rest of the image 100 outside the ROI as the quality check image. FIG. 12 depicts an example of a display 102 that shows the ROI 94 of the image 90 including the image acquired/reconstructed at the selected energy (e.g., 100 keV) and the rest of the image 100 outside the ROI as the quality check image. FIG. 13 depicts an example of a display 104 that shows the ROI 94 of the image 90 including the image acquired/reconstructed at the selected energy (e.g., 140 keV) and the rest of the image 100 outside the ROI as the quality check image. In certain embodiments, the method 80 includes changing the location of the ROI 94 by moving the mouse pointer (via the mouse) over the image 90 (block 106). The method 80 further includes receiving a user input, via a double click of a mouse button, to apply the selected keV applied to the ROI 94 to the entire image 90 (block 108).

Figure 14:
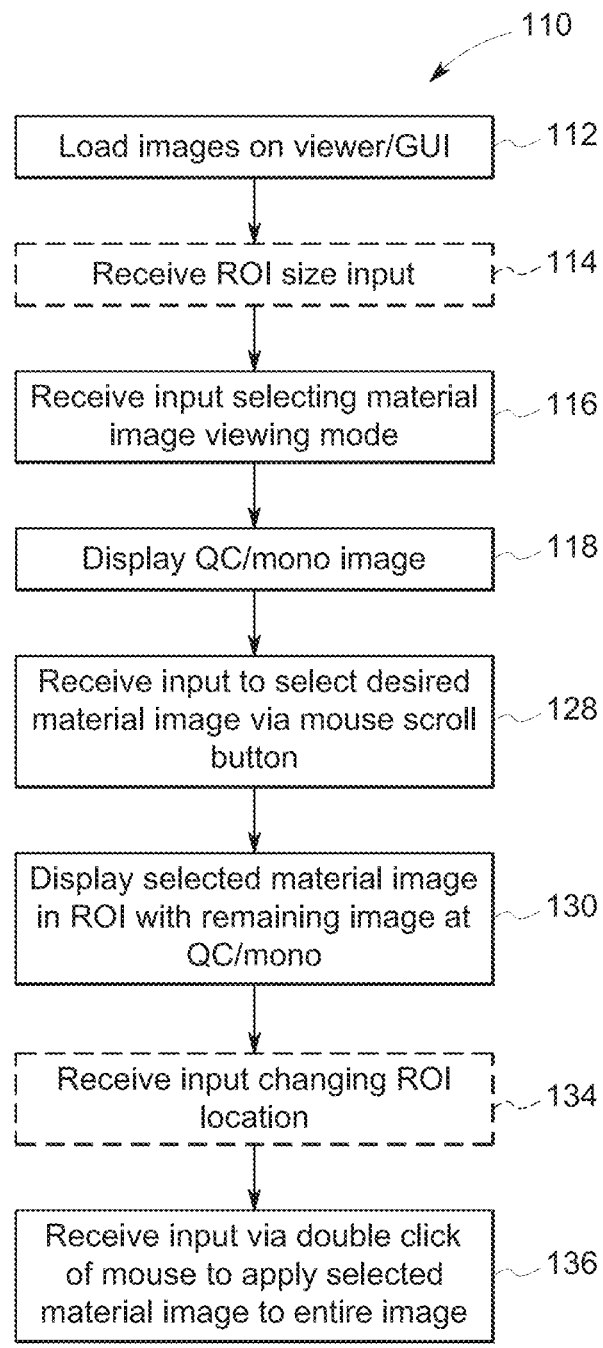
FIG. 14 is a flow chart of an embodiment of a method for optimization of image post-processing and viewing utilizing a ROI (e.g., for different material decomposition images)
Figure 15:
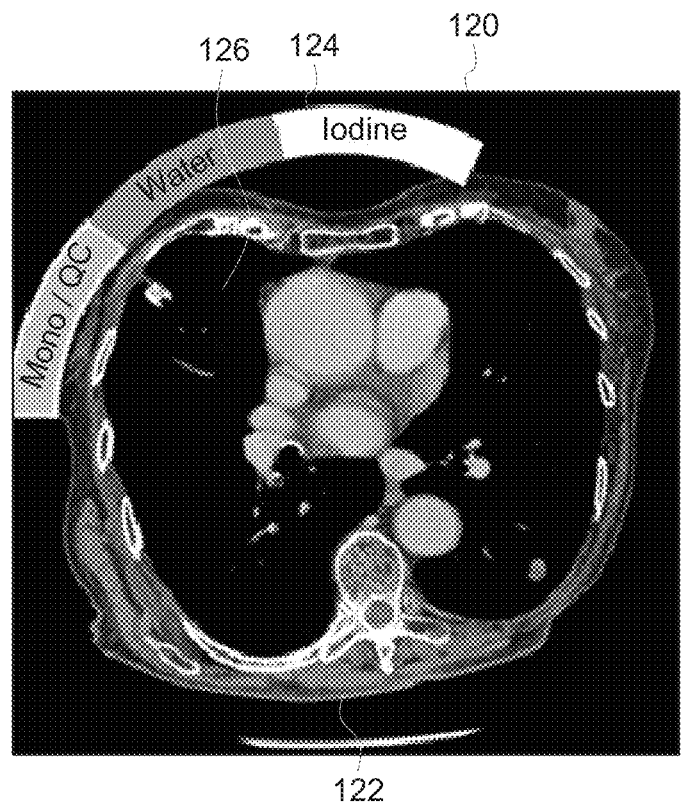
FIG. 15 is an embodiment of a display of a user interface utilizing the method of FIG. 14 (e.g., quality check/monochromatic image)

FIG. 14 is a flow chart of an embodiment of a method 110 for optimization of image post-processing and viewing utilizing a ROI (e.g., for different material decomposition images). One or more of the steps of the method 110 may be performed by the processor 12 of the system 10. One or more of the steps of method 110 may be performed simultaneously and/or in a different order from the order depicted in FIG. 14. The method 110 includes loading image data (e.g., one or more different material decomposition images) from a patient into an image viewer or GUI that enables post-processing and/or manipulation of the view of the image data (block 112). In certain embodiments, the method 110 includes receiving a user input, via the input device 18, to select or change the size of the ROI (block 114). The method 110 also includes receiving a user input, via the input device 18 selecting material decomposition or material image viewing mode for viewing the image in a mode that enables the user to select between different material decomposition images (e.g., monochromatic, water, iodine, etc.) from the same patient acquired for displaying in the ROI (block 116). As noted above, the location of the ROI on the image will be determined via the location of the mouse pointer on the image. In certain embodiments, the ROI may be displayed in a different color from the rest of the image outside the ROI. In certain embodiments, the color of the ROI of interest may vary based on the desired material being viewed (e.g., blue for water, red for iodine, etc.) for ease of analysis. The method 110 includes displaying the image (e.g., monochromatic (e.g., actual or simulated) or quality check image) in the material image viewing mode (block 118). FIG. 15 depicts an example of a display 120 of a user interface displaying the image 122. The image 122 in FIG. 15 depicts a monochromatic or quality check image. A scale 124 (e.g., material scale) representing different materials is superimposed over the image 122. A user may select a particular material (or quality check image) from the scale 124, via the scroll wheel of the mouse, to display in the ROI 126 the decomposition image for the desired material (e.g., water, iodine, etc.). The item selected on the scale 126 is highlighted. When switching between different material decomposed images, utilization of the ROI may enable the user to better identify a malignant or benign tumor. As depicted in FIG. 15, monochromatic/QC (quality check) is selected on the scale 124. Thus, the ROI 126 also displays the monochromatic or quality check image.

Figure 16:
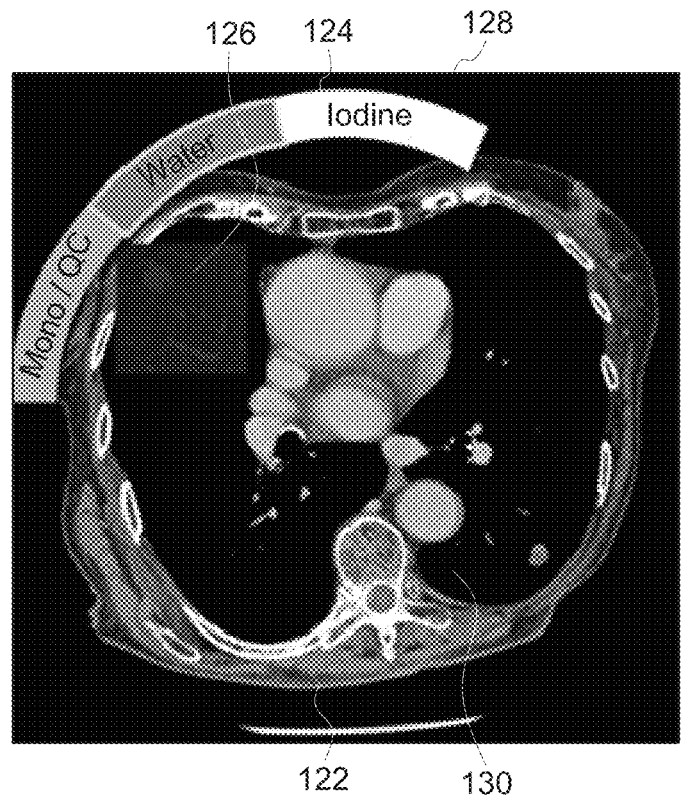
FIG. 16 is an embodiment of a display of a user interface utilizing the method of FIG. 14 (e.g., water image)
Figure 17:
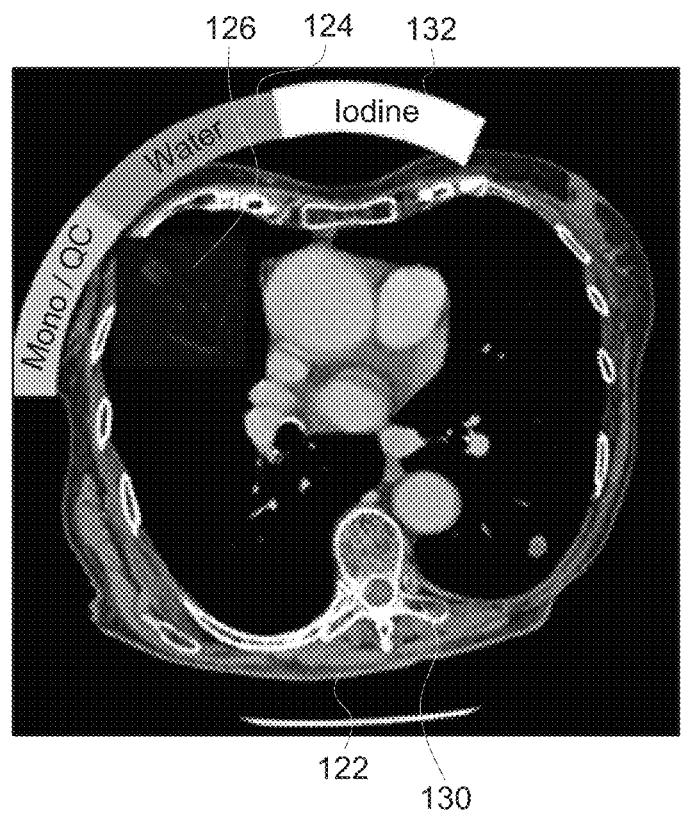
FIG. 17 is an embodiment of a display of a user interface utilizing the method of FIG. 14 (e.g., iodine image).

The method 110 includes receiving a user input, via rotation of the scroll wheel of the computer mouse, to change the desired material on the scale 124 (block 128). The item selected on the scale 124 is highlighted. The method 110 also includes displaying only in the ROI 126 the selected material decomposition image of the patient while the rest of the image remains the monochromatic or quality check image (block 130). FIG. 16 depicts an example of a display 128 that shows the ROI 126 of the image 122 including the water decomposition image and the rest of the image 130 outside the ROI as the monochromatic or quality check image. FIG. 17 depicts an example of a display 132 that shows the ROI 126 of the image 122 including the iodine decomposition image and the rest of the image 130 outside the ROI as the monochromatic or quality check image. In certain embodiments, the method 110 includes changing the location of the ROI 126 by moving the mouse pointer (via the mouse) over the image 122 (block 134). The method 110 further includes receiving a user input, via a double click of a mouse button, to apply the selected material decomposition applied to the ROI 126 to the entire image 122 (block 136).

The embodiments described above may include additional features. In certain embodiments, the image quality of the image outside of the ROI may remain the same while the image quality is altered for the ROI. This may assist the user in carefully examining the ROI. For example, if the entire image is low pass filtered and the ROI is high pass filtered, the user may better visualize the edges within the ROI without being obscured by the information from the remaining image. Also, a window width and window length of the ROI may be adjusted without altering the rest of the image. In certain embodiments, in the filtering mode, multiple ROI may be utilized with each using a different filter.

Technical effects of the disclosed embodiments include providing an optimized workflow for image post-processing and viewing that utilizes a ROI of the image. In certain embodiments, once an image is loaded into an image viewer or user interface a user (e.g., radiologist) may utilize a user input device (e.g., mouse) to optimize the workflow (e.g., ROI based workflow) in performing post-processing procedures and/or altering the view of the image. Utilization of the ROI in conjunction with manipulation of the mouse enables an improvement in the workflow time.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
utilizing a processor to:
load image data on a user interface;
receive a first input selecting a particular mode to view the image data in on the user interface that causes display of an image derived from the image data on the user interface on a display;
receive a second input, via a scroll wheel of a computer mouse, selecting a type of image that causes display in only a region of interest (ROI) of the selected type of image on the user interface on the display while a remainder of the image outside the ROI is displayed at a default state; and
receive a third input, via a button of the computer mouse, that causes application of the selected type of image to the entire image displayed on the user interface on the display.

2. The method of claim 1, comprising utilizing the processor to receive an additional input on the user interface that causes a change in size of the ROI.

3. The method of claim 1, comprising utilizing the processor to receive an additional input on the user interface that causes a change in location of the ROI on the image.

4. The method of claim 1, wherein the particular mode comprises application of an initial filter to the ROI of the image.

5. The method of claim 4, wherein selecting the type of image comprises changing the initial or a current filter applied to the ROI to a different filter that is applied to the ROI.

6. The method claim 5, wherein receiving the third input causes a currently selected filter applied to the ROI to be applied to the entire image.

7. The method of claim 1, wherein the particular mode comprises an energy acquisition/reconstruction mode that enables switching between different images acquired or reconstructed from the same patient at different energies for display in only the ROI while the remainder of the image outside the ROI displays a quality check image.

8. The method of claim 7, wherein selecting the type of image comprises changing the initial or a current image displayed in the ROI acquired or reconstructed at a particular energy to a different image acquired or reconstructed at a different energy.

9. The method of claim 8, wherein receiving the third input causes a currently displayed image acquired or reconstructed at a specific energy displayed in the ROI to be displayed for the entire image.

10. The method of claim 1, wherein the particular mode comprises a material decomposition mode that enables switching between different material decomposition images acquired from the same patient for different materials for display in only the ROI while the remainder of the image outside the ROI displays a quality check image or a monochromatic image.

11. The method of claim 10, wherein the selecting the type of image comprises changing the initial or a current image displayed in the ROI for a particular material to a different image for a different material.

12. The method of claim 11, wherein receiving the third input causes a currently displayed image for a specific material displayed in the ROI to be displayed for the entire image.

13. A non-transitory computer-readable medium, the computer-readable medium comprising processor-executable code to:
load image data on a user interface;
receive a first input selecting a particular mode to view the image data in on the user interface that causes display of an image derived from the image data on the user interface on a display;
receive a second input, via a scroll wheel of a computer mouse, selecting a type of image that causes display in only a region of interest (ROI) of the selected type of image on the user interface on the display while a remainder of the image outside the ROI is displayed at a default state; and
receive a third input, via a button of the computer mouse, that causes application of the selected type of image to the entire image displayed on the user interface on the display.

14. The non-transitory computer-readable medium of claim 13, wherein the particular mode comprises an energy acquisition/reconstruction mode that enables switching between different images acquired or reconstructed from the same patient at different energies for display in only the ROI while the remainder of the image outside the ROI displays a quality check image.

15. The non-transitory computer-readable medium of claim 14, wherein selecting the type of image comprises changing the initial or a current image displayed in the ROI acquired or reconstructed at a particular energy to a different image acquired at a different energy.

16. The non-transitory computer-readable medium of claim 15, wherein receiving the third input causes a currently displayed image acquired or reconstructed at a specific energy displayed in the ROI to be displayed for the entire image.

17. The non-transitory computer-readable medium of claim 13, wherein the particular mode comprises a material decomposition mode that enables switching between different material decomposition images acquired from the same patient for different materials for display in only the ROI while the remainder of the image outside the ROI displays a quality check image or a monochromatic image.

18. The non-transitory computer-readable medium of claim 17, wherein the selecting the type of image comprises changing the initial or a current image displayed in the ROI for a particular material to a different image for a different material.

19. The non-transitory computer-readable medium of claim 18, wherein receiving the third input causes a currently displayed image for a specific material displayed in the ROI to be displayed for the entire image.

20. A system, comprising:
a display;
a processor; and
a memory storing processor-executable code that when executed by the processor causes:

loading image data on a user interface;
receiving a first input selecting a particular mode to view the image data in on the user interface that causes display of an image derived from the image data on the user interface on the display;
receiving a second input, via a scroll wheel of a computer mouse, selecting a type of image that causes display in only a region of interest (ROI) of the selected type of image on the user interface on the display while a remainder of the image outside the ROI is displayed at a default state; and
receiving a third input, via a button of the computer mouse, that causes application of the selected type of image to the entire image displayed on the user interface on the display.

* * * * *